US007792241B2

(12) United States Patent
Wu et al.

(10) Patent No.: US 7,792,241 B2
(45) Date of Patent: Sep. 7, 2010

(54) SYSTEM AND METHOD OF FAST KVP SWITCHING FOR DUAL ENERGY CT

(75) Inventors: Xiaoye Wu, Rexford, NY (US); David Langan, Clifton Park, NY (US); Colin R. Wilson, Niskayuna, NY (US); Yun Zou, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 44 days.

(21) Appl. No.: 12/257,658

(22) Filed: Oct. 24, 2008

(65) Prior Publication Data

US 2010/0104062 A1 Apr. 29, 2010

(51) Int. Cl.
*A61B 6/00* (2006.01)

(52) U.S. Cl. .......................... 378/16; 378/114; 378/137

(58) Field of Classification Search ............... 378/4–20, 378/101, 114, 119, 121, 136, 137, 138
See application file for complete search history.

(56) References Cited

U.S. PATENT DOCUMENTS 3,946,261 A 3/1976 Holland et al. .............. 378/134
4,109,151 A 8/1978 Pleil .......................... 378/98.2
4,541,106 A 9/1985 Belanger et al. ......... 378/98.11
4,799,248 A 1/1989 Furbee et al. ............... 378/114
2004/0247082 A1* 12/2004 Hoffman .................... 378/119
2007/0041490 A1 2/2007 Jha et al. ....................... 378/8

FOREIGN PATENT DOCUMENTS

WO 2007017773 A3 2/2007

* cited by examiner

*Primary Examiner*—Courtney Thomas
(74) *Attorney, Agent, or Firm*—Jason K. Klindtworth

(57) ABSTRACT

A CT system includes a rotatable gantry having an opening for receiving an object to be scanned and an x-ray source coupled to the gantry and configured to project x-rays through the opening. The x-ray source includes a target, a first cathode configured to emit a first beam of electrons toward the target, a first gridding electrode coupled to the first cathode, a second cathode configured to emit a second beam of electrons toward the target, and a second gridding electrode coupled to the second cathode. The system includes a generator configured to energize the first cathode to a first kVp and to energize the second cathode to a second kVp, and a detector attached to the gantry and positioned to receive x-rays that pass through the opening. The system also includes a controller configured to apply a gridding voltage to the first gridding electrode to block emission of the first beam of electrons toward the target, apply the gridding voltage to the second gridding electrode to block emission of the second beam of electrons toward the target, and acquire dual energy imaging data from the detector.

19 Claims, 9 Drawing Sheets

SYSTEM AND METHOD OF FAST KVP SWITCHING FOR DUAL ENERGY CT

BACKGROUND OF THE INVENTION

The present invention relates generally to diagnostic imaging and, more particularly, to an apparatus and method of acquiring imaging data at more than one energy range using a multi-energy imaging source.

Typically, in computed tomography (CT) imaging systems, an x-ray source emits a fan-shaped or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis, which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

A CT imaging system may include an energy sensitive (ES), multi-energy (ME), and/or dual-energy (DE) CT imaging system that may be referred to as an ESCT, MECT, and/or DECT imaging system, in order to acquire data for material decomposition or effective Z estimation. Such systems may use a scintillator or a direct conversion detector material in lieu of the scintillator. The ESCT, MECT, and/or DECT imaging system in an example is configured to be responsive to different x-ray spectra. For example, a conventional third-generation CT system may acquire projections sequentially at different peak kilovoltage (kVp) operating levels of the x-ray tube, which changes the peak and spectrum of energy of the incident photons comprising the emitted x-ray beams. Energy sensitive detectors may be used such that each x-ray photon reaching the detector is recorded with its photon energy.

Techniques to obtain energy sensitive measurements comprise: (1) scan with two distinctive energy spectra, and (2) detect photon energy according to energy deposition in the detector. ESCT/MECT/DECT provides energy discrimination and material characterization. For example, in the absence of object scatter, the system derives the behavior at a different energy based on the signal from two relative regions of photon energy from the spectrum: the low-energy and the high-energy portions of the incident x-ray spectrum. In a given energy region relevant to medical CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object composed of two hypothetical materials, or the effective atomic number distribution with the scanned object.

A principle objective of energy sensitive scanning is to obtain diagnostic CT images that enhance information (contrast separation, material specificity, etc.) within the image by utilizing two scans at different chromatic energy states. A number of techniques have been proposed to achieve energy sensitive scanning including acquiring two scans either (1) back-to-back sequentially in time where the scans require two rotations of the gantry around the subject, or (2) interleaved as a function of the rotation angle requiring one rotation around the subject, in which the tube operates at, for instance, 80 kVp and 140 kVp potentials. High frequency generators have made it possible to switch the kVp potential of the high frequency electromagnetic energy projection source on alternating views. As a result, data for two energy sensitive scans may be obtained in a temporally interleaved fashion rather than two separate scans made several seconds apart as required with previous CT technology.

However, taking separate scans several seconds apart from one another may result in mis-registration between datasets caused by patient motion (both external patient motion and internal organ motion) and different cone angles. And, in general, a conventional two-pass dual kVp technique cannot be applied reliably where small details need to be resolved for body features that are in motion.

Another technique to acquire projection data for material decomposition includes using energy sensitive detectors, such as a CZT or other direct conversion material having electronically pixelated structures or anodes attached thereto. However, this technology typically has a low saturation flux rate that may be insufficient, and the maximum photon-counting rate achieved by the current technology may be two or more orders of magnitude below what is necessary for general-purpose medical CT applications.

Therefore, it would be desirable to design an apparatus and method of fast switching between energy levels and acquiring imaging data at more than one energy range.

BRIEF DESCRIPTION OF THE INVENTION

Embodiments of the invention are directed to a method and apparatus for acquiring imaging data at more than one energy range that overcome the aforementioned drawbacks.

A dual energy CT system and method is disclosed. Embodiments of the invention support the acquisition of both anatomical detail as well as tissue characterization information for medical CT, and for components within luggage. Energy discriminatory information or data may be used to reduce the effects of beam hardening and the like. The system supports the acquisition of tissue discriminatory data and therefore provides diagnostic information that is indicative of disease or other pathologies. This detector can also be used to detect, measure, and characterize materials that may be injected into the subject such as contrast agents and other specialized materials by the use of optimal energy weighting to boost the contrast of iodine and calcium (and other high atomic or materials). Contrast agents can, for example, include iodine that is injected into the blood stream for better visualization. For baggage scanning, the effective atomic number generated from energy sensitive CT principles allows reduction in image artifacts, such as beam hardening, as well as provides addition discriminatory information for false alarm reduction.

According to an aspect of the invention, a CT system includes a rotatable gantry having an opening for receiving an object to be scanned and an x-ray source coupled to the gantry and configured to project x-rays through the opening. The x-ray source includes a target, a first cathode configured to emit a first beam of electrons toward the target, a first gridding electrode coupled to the first cathode, a second cathode configured to emit a second beam of electrons toward the target, and a second gridding electrode coupled to the second cathode. The system includes a generator configured to energize the first cathode to a first kVp and to energize the second cathode to a second kVp, and a detector attached to the gantry and positioned to receive x-rays that pass through the opening. The system also includes a controller configured to apply a gridding voltage to the first gridding electrode to block emission of the first beam of electrons toward the target, apply the gridding voltage to the second gridding electrode to block emission of the second beam of electrons toward the target, and acquire dual energy imaging data from the detector.

According to another aspect of the invention, a method of acquiring energy sensitive CT imaging data includes applying a first voltage potential between a first cathode and an x-ray target and applying a second voltage potential between a second cathode and the x-ray target while the first voltage potential is applied between the first cathode and the x-ray target, wherein the second voltage potential is different from the first voltage potential. The method further includes interrupting emission of electrons from the first cathode to the x-ray target, obtaining a first set of imaging data from x-rays generated via the second voltage potential, and reconstructing an image from acquired imaging data, wherein the acquired imaging data comprises the first set of imaging data.

According to yet another aspect of the invention, a computer readable storage medium having stored thereon a computer program comprising instructions which when executed by a computer cause the computer to apply a first kVp potential between a first cathode and a target and apply a second kVp potential between a second cathode and the target. The computer is further caused to alternate application of a gridding voltage to the first cathode and to the second cathode to alternately prevent electrons from traversing a respective one of the first and second kVp potentials and reconstruct an image from x-rays generated at the first and second kVps.

These and other advantages and features will be more readily understood from the following detailed description of preferred embodiments of the invention that is provided in connection with the accompanying drawings.

DETAILED DESCRIPTION OF THE PREFERRED EMBODIMENT

Diagnostics devices comprise x-ray systems, magnetic resonance (MR) systems, ultrasound systems, computed tomography (CT) systems, positron emission tomography (PET) systems, ultrasound, nuclear medicine, and other types of imaging systems. Applications of x-ray sources comprise imaging, medical, security, and industrial inspection applications. However, it will be appreciated by those skilled in the art that an implementation is applicable for use with single-slice or other multi-slice configurations. Moreover, an implementation is employable for the detection and conversion of x-rays. However, one skilled in the art will further appreciate that an implementation is employable for the detection and conversion of other high frequency electromagnetic energy. An implementation is employable with a "third generation" CT scanner and/or other CT systems.

The operating environment of the present invention is described with respect to a sixty-four-slice computed tomography (CT) system. However, it will be appreciated by those skilled in the art that the present invention is equally applicable for use with other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
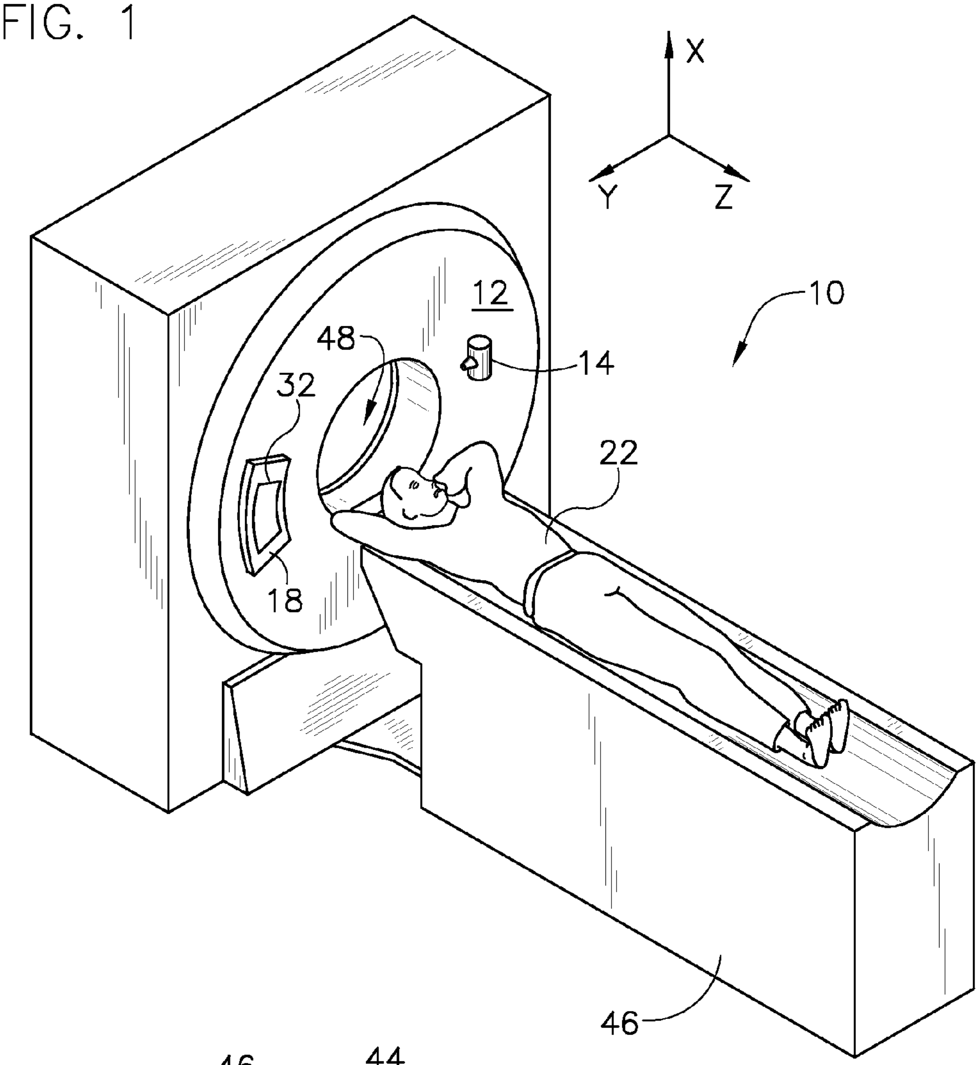
FIG. 1 is a pictorial view of a CT imaging system.
Figure 2:
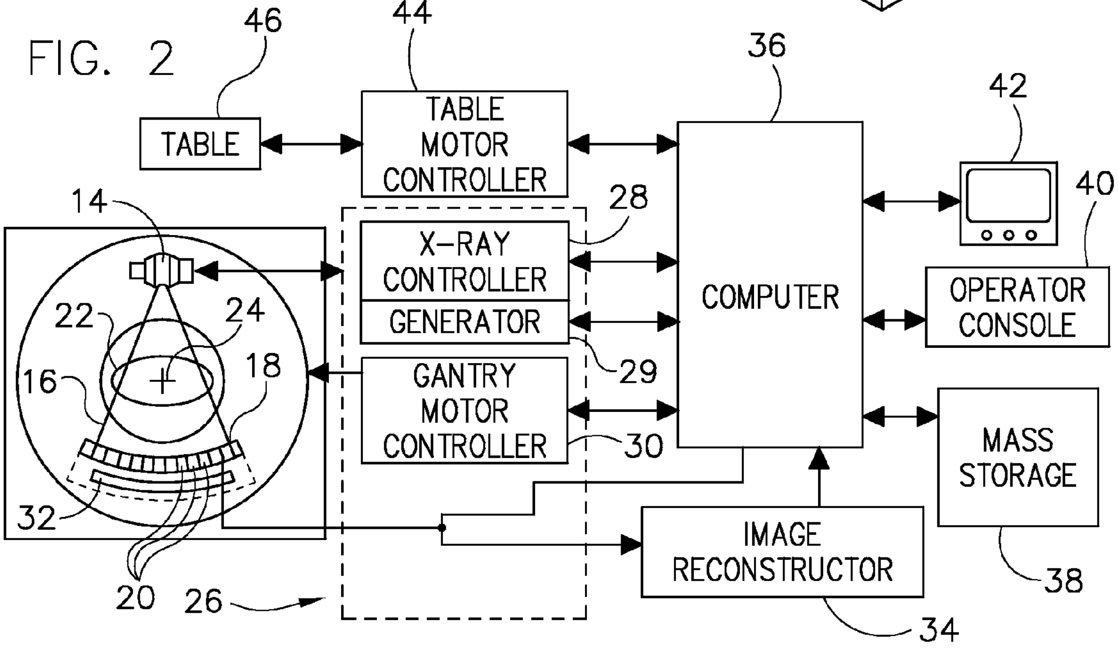
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. In embodiments of the invention, x-ray source 14 includes either a stationary target or a rotating target. Referring now to FIG. 2, detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 and generator 29 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

System 10 may be operated in either monopolar or bipolar modes. In monopolar operation, either the anode is grounded and a negative potential is applied to the cathode, or the cathode is grounded and a positive potential is applied to the anode. Conversely, in bipolar operation, an applied potential is split between the anode and the cathode. In either case, monopolar or bipolar, a potential is applied between the anode and cathode, and electrons emitting from the cathode are caused to accelerate, via the potential, toward the anode. When, for instance, a −140 kV voltage differential is maintained between the cathode and the anode and the tube is a bipolar design, the cathode may be maintained at, for instance, −70 kV, and the anode may be maintained at +70 kV. In contrast, for a monopolar design having likewise a −140 kV standoff between the cathode and the anode, the cathode accordingly is maintained at this higher potential of −140 kV while the anode is grounded and thus maintained at approximately 0 kV. Accordingly, the anode is operated having a net 140 kV difference with the cathode within the tube.

Figure 3:
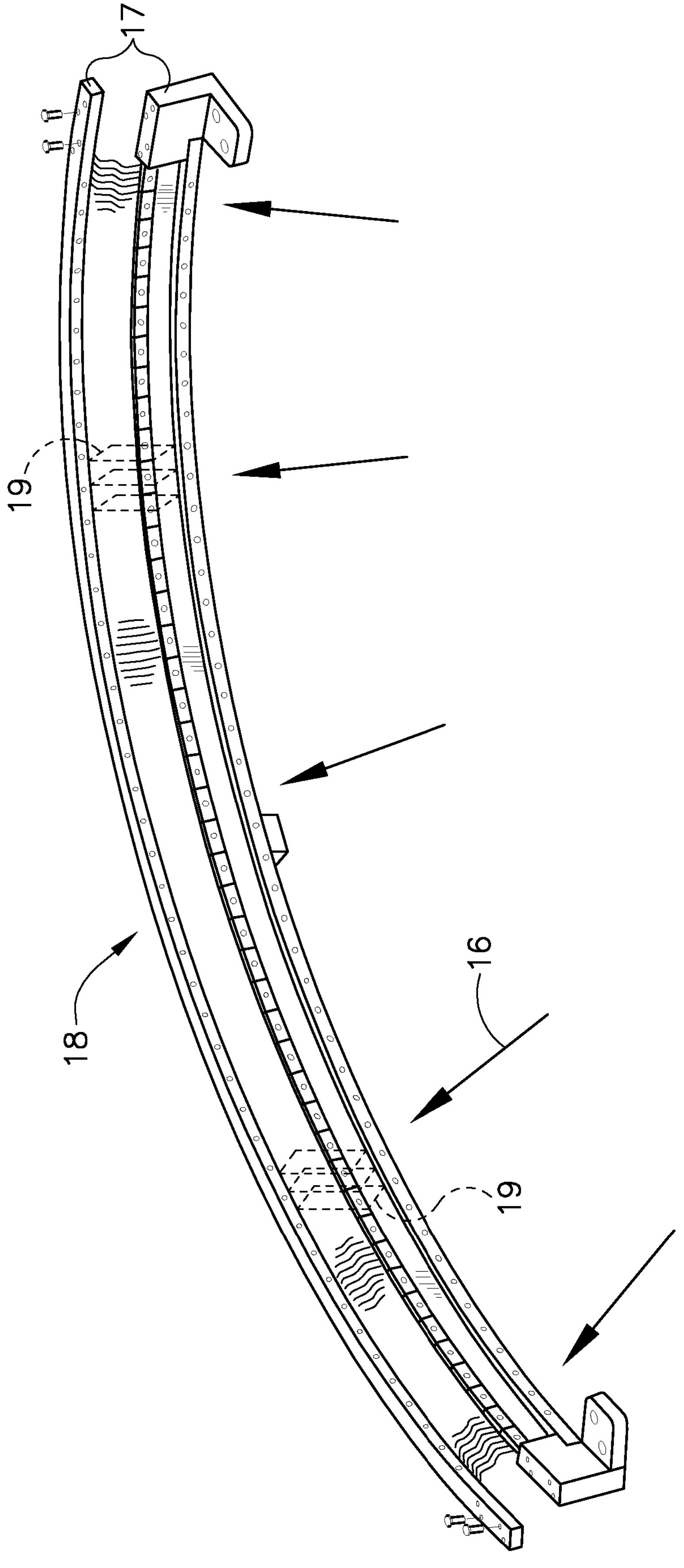
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
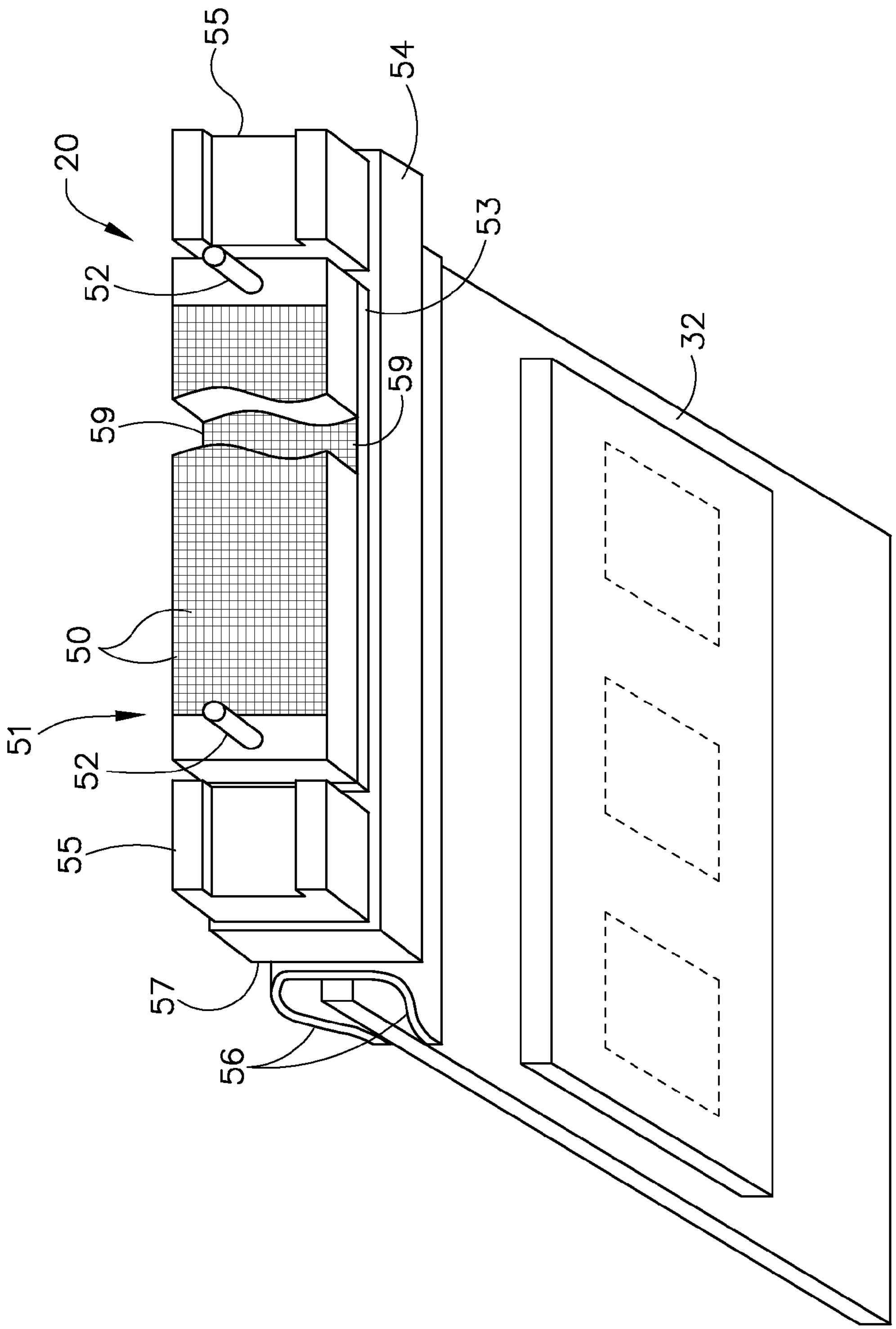
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

Figure 5:
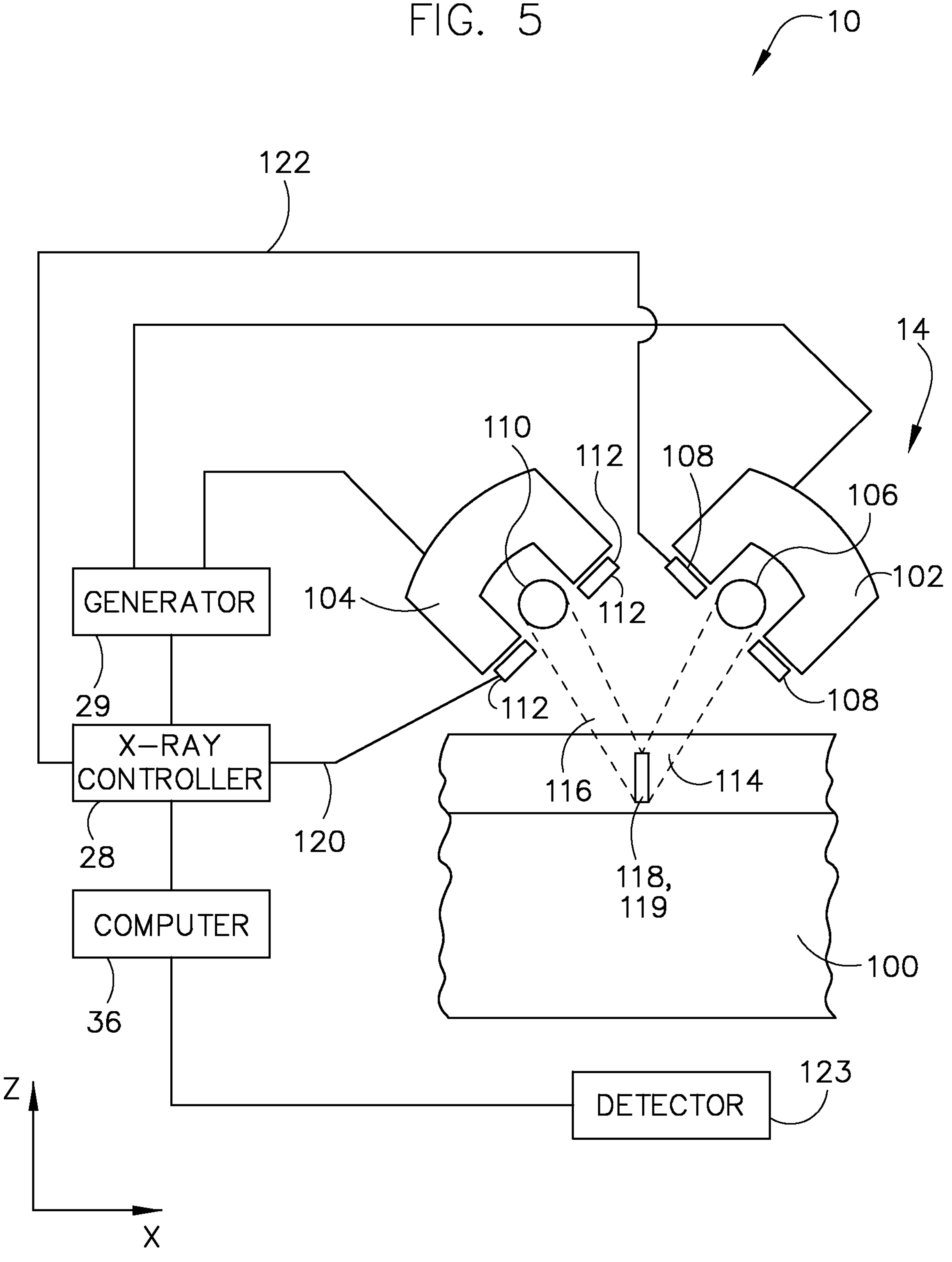
FIG. 5 is an illustration of a two cathode x-ray tube according to an embodiment of the invention.

FIG. 5 illustrates an embodiment of system 10 shown in FIGS. 1 and 2. System 10, as discussed, includes x-ray source 14, x-ray controller 28, generator 29, and computer 36. X-ray source 14 includes a target 100 (illustrated from a point of view of an edge of the target) and first and second cathodes 102, 104. First cathode 102 includes a first filament 106 and a pair of mA gridding electrodes 108. Second cathode 104, likewise, includes a second filament 110 and a pair of mA gridding electrodes 112. Cathode 102 is positioned to emit a first beam of electrons 114 from first filament 106 toward a focal spot 118, and cathode 104 is positioned to emit a second beam of electrons 116, in this embodiment, toward a focal spot 119. In the embodiment illustrated, focal spot 118 and focal spot 119 are coincident and impinge the target at substantially the same position with respect to a rotational axis (not shown) of the target 100. First and second filaments 106, 110 may be the same size or may be differently sized to generate same or different focal spot sizes. Each cathode 102, 104 is configured to have a gridding voltage applied thereto. The mA gridding electrodes 108 of first cathode 102 are coupled to x-ray controller 28 via a line 120, and mA gridding electrodes 112 of second cathode 104 are coupled to x-ray controller 28 via a line 122. Gridding voltages applied to mA gridding electrodes 108, 112, may range from a few hundred volts to a few thousand volts.

Figure 6:
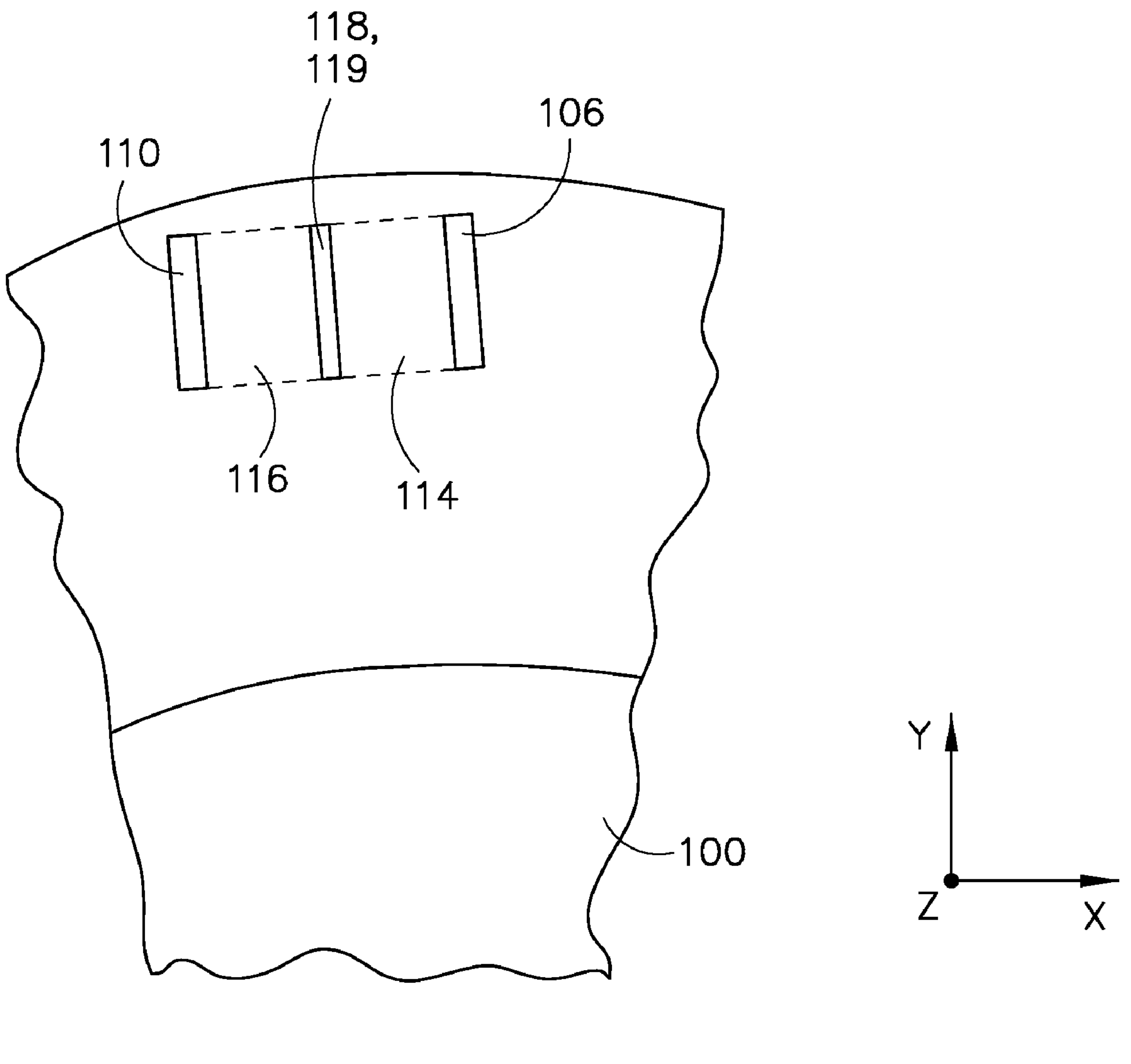
FIG. 6 is a plan view of an x-ray tube target according to one embodiment of the invention.
Figure 7:
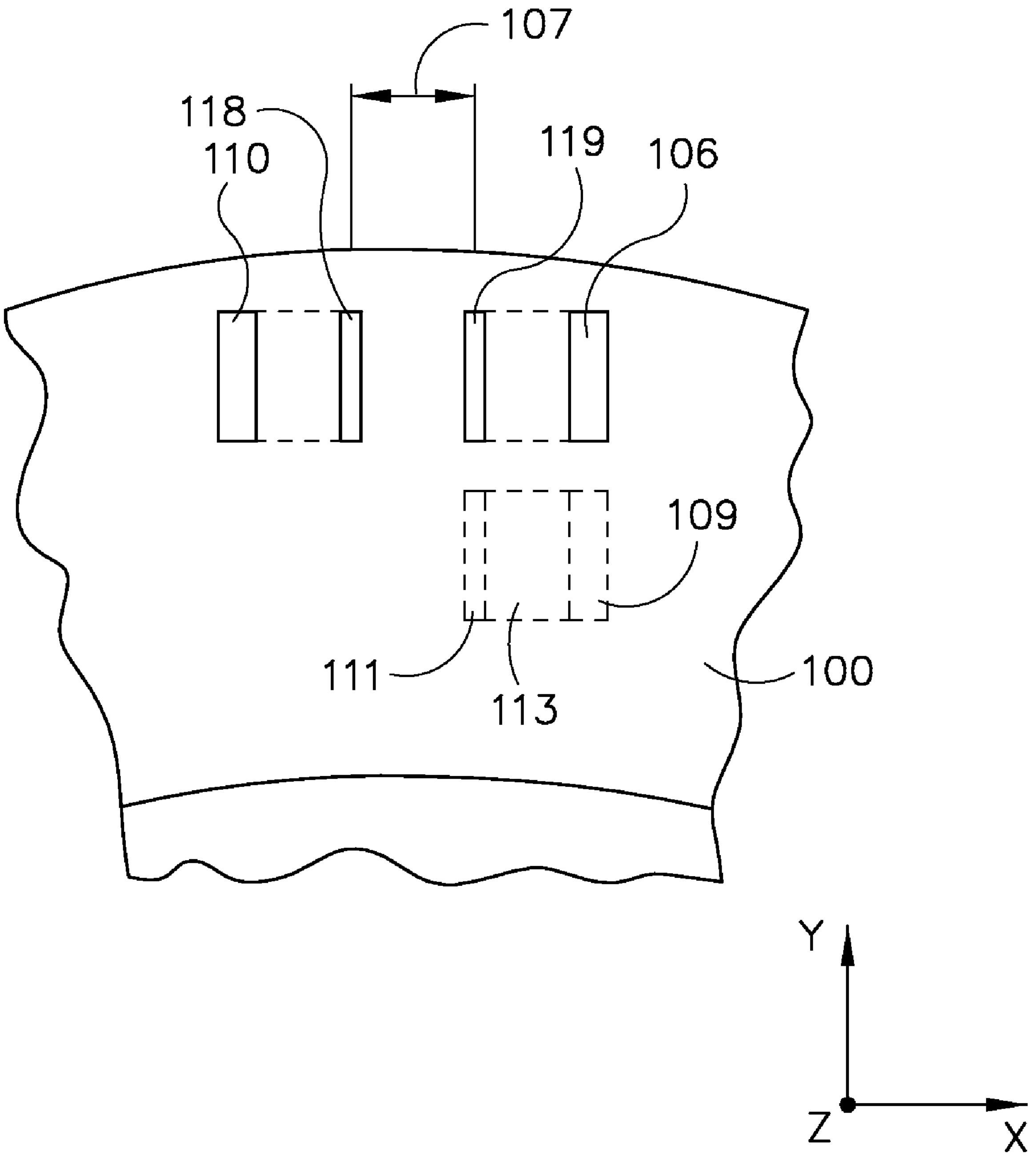
FIG. 7 is a plan view of an x-ray tube target according to one embodiment of the invention.

FIGS. 6 and 7 graphically illustrate plan views of target 100 and first and second filaments 106, 110 according to embodiments of the invention. FIG. 6 illustrates first and second filaments 106, 110 positioned in cathodes (not shown), such as cathodes 102, 104 of FIG. 5, such a that respective first and second beams of electrons 114, 116 impinge the target 100 at coincident spots 118, 119, as illustrated in FIG. 5. FIG. 7 illustrates another embodiment where the cathodes (not shown) and respective first and second filaments 106, 110 are separated such that focal spots 118, 119 do not impinge the target at substantially the same location with respect to a rotational axis (not shown) of the target 100, but are instead offset by a distance 107 in an X direction. In addition, FIG. 7 also illustrates an optional focal spot position 111 such that x-rays that emit therefrom are offset in a Z direction with respect to second filament 110. As illustrated in phantom, instead of offsetting only in an X direction, first filament 106 may also be offset to position 109 such that focal spot 111 is impinged by beam of electrons 113 that emit from the first filament 106 when positioned at position 109. According to that shown in FIGS. 6 and 7, embodiments of the invention include emitting x-rays from the same spot location as shown in FIG. 6 or from locations offset in X and/or Z directions, respectively, as illustrated in FIG. 7.

Figure 8:
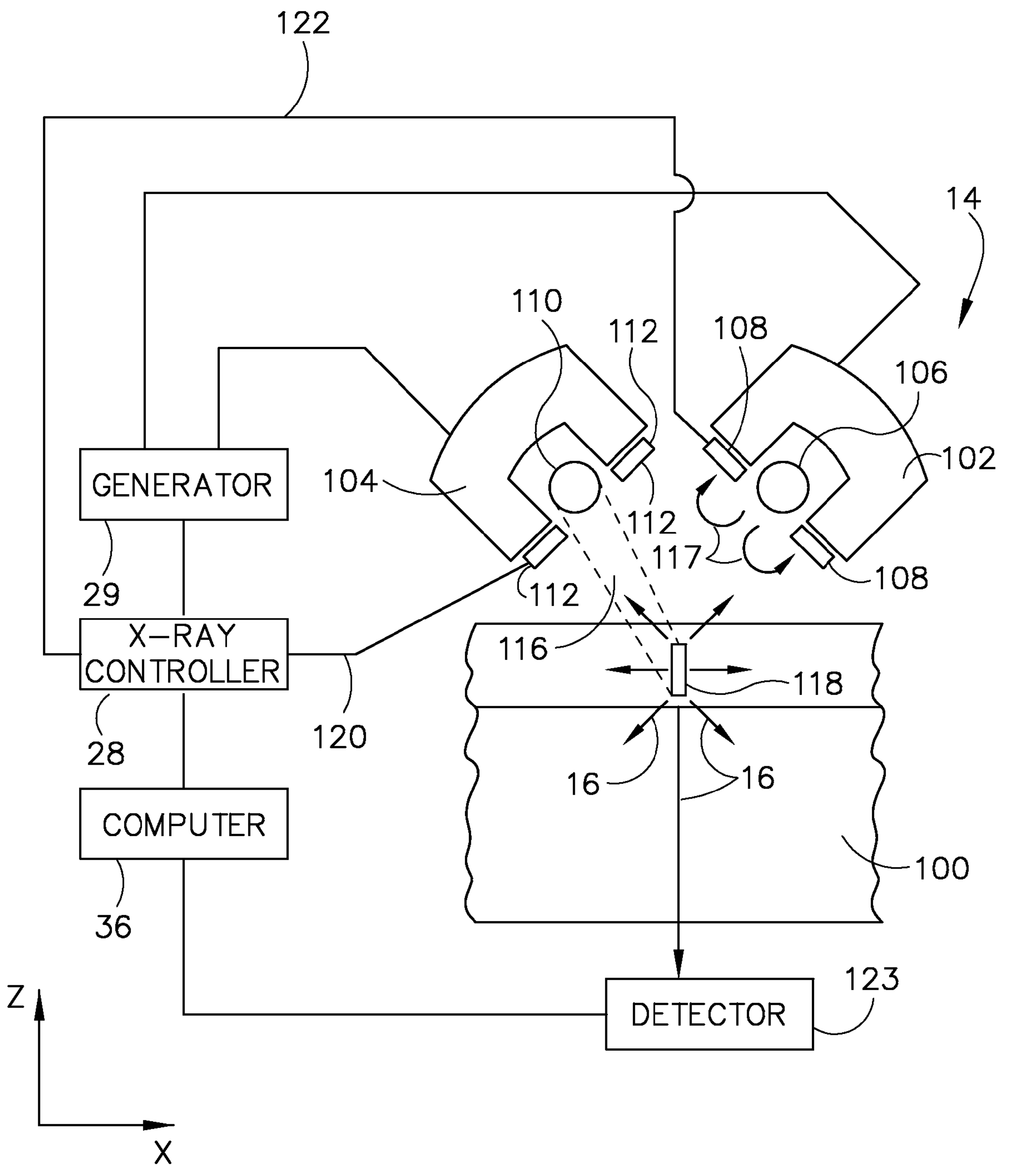
FIGS. 8 and 9 illustrate operation of the embodiment illustrated in FIG. 5.
Figure 9:
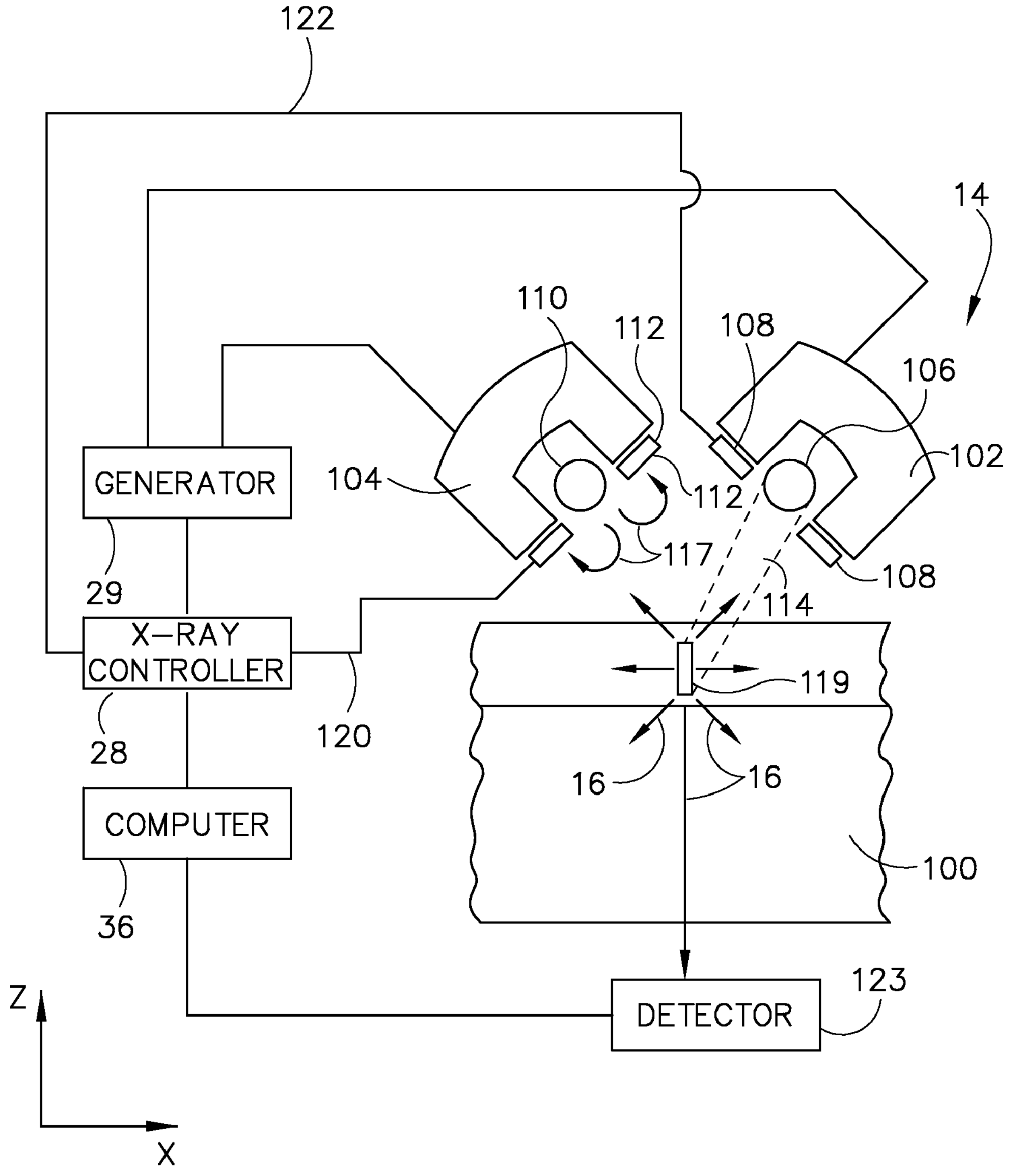

FIGS. 8 and 9 graphically show application of a gridding voltage alternately between gridding electrodes 108 and gridding electrodes 112. As illustrated in FIG. 8, x-ray controller 28 causes a first voltage potential to be applied between first cathode 102 and target 100 via generator 29. X-ray controller 28 simultaneously causes a second voltage potential to be applied between second cathode 104 and target 100 via generator 29. In one embodiment, the first voltage is 80 kVp and the second voltage is 140 kVp. X-ray controller 28 applies a gridding voltage to gridding electrodes 108. First filament 106 emits electrons 117 during application of the gridding voltage to gridding electrodes 108, but the gridding voltage redirects electrons 117 emitting from first filament 106 back toward the cathode 102. As such, the gridding voltage blocks or interrupts emission of electrons 117 to target 100. Because there is no gridding voltage applied to gridding electrodes 112 of second cathode 104, electrons 116 are caused to emit from second filament 110 and are accelerated across the second voltage potential toward target 100 and, more specifically, toward focal spot 118, where x-rays 16 having a second energy are generated therefrom.

In a next step of operation as illustrated in FIG. 9, x-ray controller 28 causes a gridding voltage to be applied to gridding electrodes 112 of second cathode 104 while removing application of the gridding voltage from gridding electrodes 108 of first cathode 102. As such, gridding electrodes 112, having a gridding voltage applied thereto, cause electrons 119 that are emitted from second filament 110 to emit back toward cathode 104 to block or interrupt emission of electrons 119 to target 100. Because there is no gridding voltage applied to gridding electrodes 108 of first cathode 102, electrons 114 are caused to emit from first filament 106 and are accelerated across the first voltage potential toward target 100 and, more specifically, toward focal spot 119, where x-rays 16 having a first energy are generated therefrom.

X-ray controller 28 rapidly and alternatingly applies gridding voltages to gridding electrodes 108, 112 via, respectively, lines 120, 122 as illustrated in FIGS. 8 and 9 while rapidly and alternatingly acquiring imaging data in detector 123 from x-rays 16 generated at first and second energies. Because the first and second voltage potentials are constantly applied, respectively, between each cathode 102, 104 and target 100, the rapid alternation of gridding voltages applied to gridding electrodes 108, 122 causes electrons 114, 116 to respectively emit in a likewise rapidly alternating fashion, thus causing x-rays 16 to emit from the focal spots 119, 118 that are generated at the first voltage, and then at the second voltage. As such, x-ray source 14 is able to generate x-rays at two voltage levels, thus allowing system 10 to acquire dual energy imaging data from x-rays that are rapidly alternated between high and low kVps. As such, the image reconstructor 34 of FIG. 2 may then acquire the imaging data as projection data and reconstruct an image using the dual energy data acquired the high and low kVps.

X-ray controller 28 may simultaneously, during operation, remove application of the gridding voltages from both sets of gridding electrodes 108, 112. Thus, when no gridding voltages are applied, electron beams 114 and 116 may be caused to simultaneously emit from respective first and second filaments 106, 110 and x-rays 16 generated at focal spots 118, 119 will have x-ray spectra generated simultaneously at both first and second energies.

One skilled in the art will recognize that the gridding voltages may be applied to respective cathodes 102, 104 in synchronicity with rotation of the gantry 12 of FIGS. 1 and 2, or in synchronicity with a patient heart rate (as in a gated acquisition), as examples. As illustrated, focal spots 118, 119 may each be positioned on target 100 at the same spot with respect to a rotation axis of the target 100, from locations offset in the X, and from locations offset in both the X and Z directions. X-rays 16 may be thus rapidly generated having different energies. Because the beams 114 and 116 are independently controlled from each other, each can be turned on and off at the same time or at different times. Further, because each cathode 102, 104 includes respective gridding electrodes 108, 112 and filament heating circuits, the current, or mA, emitted from first and second filaments 106, 110 may likewise be independently controlled. Additionally, although not illustrated, focusing electrodes may be included with each cathode 102, 104 in addition to the gridding electrodes 108, 112 so that beams 114, 116 may be simultaneously gridded and focused as they emit toward target 100. In such an application, the focal spots 118, 119 may be statically positioned, or dynamically positioned, such as in a wobble application.

Figure 10:
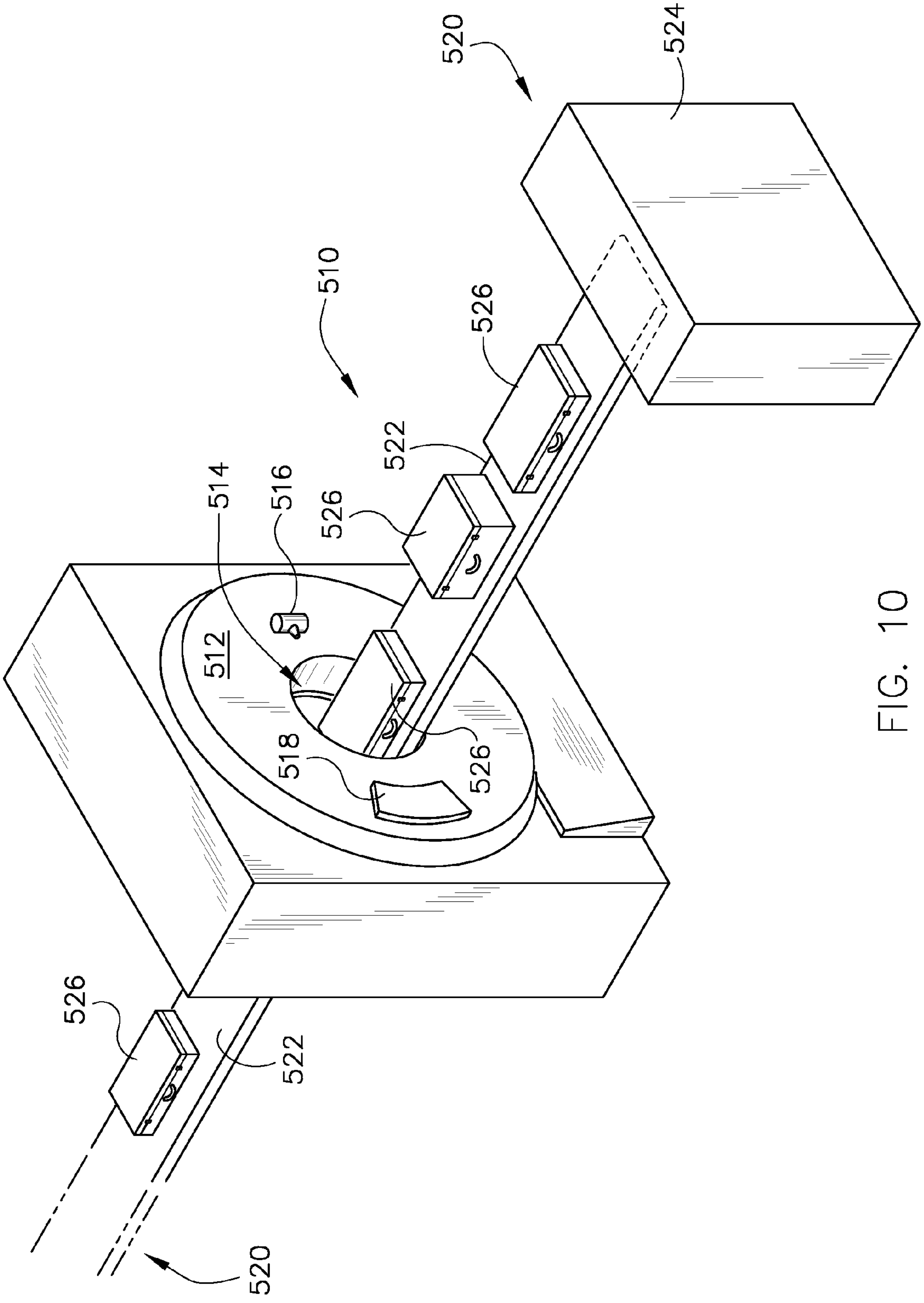
FIG. 10 is a pictorial view of a CT system for use with a non-invasive package inspection system according to an embodiment of the invention.

Referring now to FIG. 10, package/baggage inspection system 510 includes a rotatable gantry 512 having an opening 514 therein through which packages or pieces of baggage may pass. The rotatable gantry 512 houses a high frequency electromagnetic energy source 516 as well as a detector assembly 518 having scintillator arrays comprised of scintillator cells similar to that shown in FIG. 4 or 5. A conveyor system 520 also is provided and includes a conveyor belt 522 supported by structure 524 to automatically and continuously pass packages or baggage pieces 526 through opening 514 to be scanned. Objects 526 are fed through opening 514 by conveyor belt 522, imaging data is then acquired, and the conveyor belt 522 removes the packages 526 from opening 514 in a controlled and continuous manner. As a result, postal inspectors, baggage handlers, and other security personnel may non-invasively inspect the contents of packages 526 for explosives, knives, guns, contraband, etc.

An implementation of the system 10 and/or 510 in an example comprises a plurality of components such as one or more of electronic components, hardware components, and/or computer software components. A number of such components can be combined or divided in an implementation of the system 10 and/or 510. An exemplary component of an implementation of the system 10 and/or 510 employs and/or comprises a set and/or series of computer instructions written in or implemented with any of a number of programming languages, as will be appreciated by those skilled in the art. An implementation of the system 10 and/or 510 in an example comprises any (e.g., horizontal, oblique, or vertical) orientation, with the description and figures herein illustrating an exemplary orientation of an implementation of the system 10 and/or 510, for explanatory purposes.

An implementation of the system 10 and/or the system 510 in an example employs one or more computer readable signal bearing media. A computer-readable signal-bearing medium in an example stores software, firmware and/or assembly language for performing one or more portions of one or more implementations. An example of a computer-readable signal-bearing medium for an implementation of the system 10 and/or the system 510 comprises the recordable data storage medium of the image reconstructor 34, and/or the mass storage device 38 of the computer 36. A computer-readable signal-bearing medium for an implementation of the system 10 and/or the system 510 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 510, for instance, one or more of a telephone network, a local area network ("LAN"), a wide area network ("WAN"), the Internet, and/or a wireless network.

According to an embodiment of the invention, a CT system includes a rotatable gantry having an opening for receiving an object to be scanned and an x-ray source coupled to the gantry and configured to project x-rays through the opening. The x-ray source includes a target, a first cathode configured to emit a first beam of electrons toward the target, a first gridding electrode coupled to the first cathode, a second cathode configured to emit a second beam of electrons toward the target, and a second gridding electrode coupled to the second cathode. The system includes a generator configured to energize the first cathode to a first kVp and to energize the second cathode to a second kVp, and a detector attached to the gantry and positioned to receive x-rays that pass through the opening. The system also includes a controller configured to apply a gridding voltage to the first gridding electrode to block emission of the first beam of electrons toward the target, apply the gridding voltage to the second gridding electrode to block emission of the second beam of electrons toward the target, and acquire dual energy imaging data from the detector.

According to another embodiment of the invention, a method of acquiring energy sensitive CT imaging data includes applying a first voltage potential between a first cathode and an x-ray target and applying a second voltage potential between a second cathode and the x-ray target while the first voltage potential is applied between the first cathode and the x-ray target, wherein the second voltage potential is different from the first voltage potential. The method further includes interrupting emission of electrons from the first cathode to the x-ray target, obtaining a first set of imaging data from x-rays generated via the second voltage potential, and reconstructing an image from acquired imaging data, wherein the acquired imaging data comprises the first set of imaging data.

According to yet another embodiment of the invention, a computer readable storage medium having stored thereon a computer program comprising instructions which when executed by a computer cause the computer to apply a first kVp potential between a first cathode and a target and apply a second kVp potential between a second cathode and the target. The computer is further caused to alternate application of a gridding voltage to the first cathode and to the second cathode to alternately prevent electrons from traversing a respective one of the first and second kVp potentials and reconstruct an image from x-rays generated at the first and second kVps.

A technical contribution for the disclosed method and apparatus is that it provides for a computer-implemented apparatus and method of acquiring imaging data at more than one energy range using a multi-energy imaging source.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Furthermore, while single energy and dual-energy techniques are discussed above, the invention encompasses approaches with more than two energies. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A CT system comprising:

a rotatable gantry having an opening for receiving an object to be scanned;

an x-ray source coupled to the gantry and configured to project x-rays through the opening, the x-ray source comprising:

a target;

a first cathode configured to emit a first beam of electrons toward the target;

a first gridding electrode coupled to the first cathode;

a second cathode configured to emit a second beam of electrons toward the target; and a second gridding electrode coupled to the second cathode;

a generator configured to energize the first cathode to a first kVp and to energize the second cathode to a second kVp;

a detector attached to the gantry and positioned to receive x-rays that pass through the opening; and a controller configured to:

apply a gridding voltage to the first gridding electrode to block emission of the first beam of electrons toward the target;

apply the gridding voltage to the second gridding electrode to block emission of the second beam of electrons toward the target; and acquire dual energy imaging data from the detector.

2. The CT system of claim 1 wherein the controller is configured to withhold application of the gridding voltage to the second gridding electrode during application of the gridding voltage to the first gridding electrode, and wherein the controller is configured to acquire the dual energy imaging data from x-rays generated from the second beam of electrons.

3. The CT system of claim 1 wherein the generator is further configured to simultaneously energize the first and second cathodes to the first kVp and to the second kVp, respectively.

4. The CT system of claim 1 wherein the gridding voltages applied are synchronized with rotation of the rotatable gantry.

5. The CT system of claim 1 wherein the target is one of a rotating and a stationary target.

6. The CT system of claim 1 wherein the first beam of electrons is directed toward a first spot on the target, and wherein the second beam of electrons is directed toward a second spot on the target different from the first spot.

7. The CT system of claim 1 wherein the first beam of electrons and the second beam of electrons are each directed toward a same spot on the target.

8. A method of acquiring energy sensitive CT imaging data, comprising:

applying a first voltage potential between a first cathode and an x-ray target;

applying a second voltage potential between a second cathode and the x-ray target while the first voltage potential is applied between the first cathode and the x-ray target, wherein the second voltage potential is different from the first voltage potential;

interrupting emission of electrons from the first cathode to the x-ray target by applying a bias voltage to a grid positioned proximate the first cathode;

obtaining a first set of imaging data from x-rays generated via the second voltage potential; and reconstructing an image from acquired imaging data, wherein the acquired imaging data comprises the first set of imaging data.

9. The method of claim 8 further comprising:

interrupting emission of electrons from the second cathode to the x-ray target; and obtaining a second set of imaging data from x-rays generated via the first voltage potential;

wherein the acquired imaging data further comprises the second set of imaging data.

10. The method of claim 8 further comprising:

withholding interruption of electron omissions from the first and second cathodes to the x-ray target; and obtaining a second set of imaging data from x-rays generated via the first and second voltage potentials;

wherein the acquired imaging data further comprises the second set of imaging data.

11. The method of claim 8 wherein applying the first and second voltage potentials comprises generating each from the same generator.

12. The method of claim 8 wherein obtaining the first set of imaging data comprises obtaining a first set of projections of CT data from x-rays generated at the first voltage potential.

13. The method of claim 8 further comprising emitting a first beam of electrons from the first cathode to a first focal spot on the x-ray target, and emitting a second beam of electrons from the second cathode to a second focal spot on the x-ray target.

14. The method of claim 13 wherein the first focal spot and the second focal spot are coincident with one another with respect to a rotating access of the x-ray target.

15. The method of claim 13 wherein the first focal spot and the second focal spot are at different locations with respect to a rotating access of the x-ray target.

16. A computer readable storage medium having stored thereon a computer program comprising instructions which when executed by a computer cause the computer to:

apply a first kVp potential between a first cathode and a target;

apply a second kVp potential between a second cathode and the target;

alternate application of a gridding voltage to the first cathode and to the second cathode to alternately prevent electrons from traversing a respective one of the first and second kVp potentials; and reconstruct an image from x-rays generated at the first and second kVps.

17. The computer readable storage medium of claim 16 wherein the computer is further caused to:

acquire imaging data from x-rays generated from electrons traversing the first kVp potential while application of the gridding voltage is applied to the second cathode; and acquire imaging data from x-rays generated from electrons traversing the second kVp potential while application of the gridding voltage is applied to the first cathode.

18. The computer readable storage medium of claim 16 wherein the computer is further caused to apply the first kVp potential simultaneously with application of the second kVp potential.

19. The computer readable storage medium of claim 16 wherein the computer is further caused to:

acquire a first projection of imaging data from x-rays generated from electrons traversing the first kVp potential; and acquire a second projection of imaging data from x-rays generated from electrons traversing the second kVp potential.

* * * * *